(12) United States Patent
Berberich et al.

(10) Patent No.: US 12,419,628 B2
(45) Date of Patent: Sep. 23, 2025

(54) BONE ANCHORING ASSEMBLY

(71) Applicant: MEDACTA INTERNATIONAL SA, Castel San Pietro (CH)

(72) Inventors: Sascha Berberich, Castel San Pietro (CH); Francesco Siccardi, Castel San Pietro (CH); Matteo Ponzoni, Castel San Pietro (CH); Riccardo Lucchini, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 506 days.

(21) Appl. No.: 17/598,094

(22) PCT Filed: Mar. 26, 2020

(86) PCT No.: PCT/IB2020/052859
§ 371 (c)(1),
(2) Date: Sep. 24, 2021

(87) PCT Pub. No.: WO2020/194229
PCT Pub. Date: Oct. 1, 2020

(65) Prior Publication Data
US 2022/0183673 A1    Jun. 16, 2022

(30) Foreign Application Priority Data
Mar. 28, 2019 (IT) .......................... 102019000004651

(51) Int. Cl.
*A61B 17/04* (2006.01)
(52) U.S. Cl.
CPC .. *A61B 17/0401* (2013.01); *A61B 2017/0414* (2013.01); *A61B 2017/0441* (2013.01)

(58) Field of Classification Search
CPC ............................................. A61B 2017/0441
See application file for complete search history.

(56) References Cited

U.S. PATENT DOCUMENTS 6,517,542 B1 * 2/2003 Papay .................. A61C 8/0022
606/232
7,144,413 B2 * 12/2006 Wilford ................ A61F 2/0811
606/232

(Continued)

FOREIGN PATENT DOCUMENTS

JP         3171890 U       11/2011

OTHER PUBLICATIONS

English Translation of Notice of Reasons of Refusal in JP 2021-557546, mailed Aug. 17, 2022, 10 pages.

(Continued)

*Primary Examiner* — Elizabeth Houston
*Assistant Examiner* — Jonathan A Hollm
(74) *Attorney, Agent, or Firm* — Meunier Carlin & Curfman LLC

(57) ABSTRACT

Various implementations of a bone anchoring assembly comprise a bone anchor and an insert. The bone anchor comprises a proximal end, a distal end, an outer profile suitable for defining a firm and stable coupling with the bone tissue, and a seat open at the proximal end, in which the seat defines an axis. The insert defines an axis that is suitable for being received in the seat of the bone anchor and comprises a proximal end, a distal end, and one or more eyelets placed at the proximal end. Moreover, the seat and the insert comprise snap coupling means suitable for axially retaining the insert in the seat and suitable for allowing the free rotation of the insert in the seat around the axis of the insert.

6 Claims, 4 Drawing Sheets

(56) References Cited

U.S. PATENT DOCUMENTS

| | | | |
|---|---|---|---|
| 9,770,277 B2 * | 9/2017 | Biedermann | A61B 17/864 |
| 2004/0093030 A1 * | 5/2004 | Cox | A61B 17/0401 606/232 |
| 2007/0156176 A1 | 7/2007 | Fanton et al. | |
| 2008/0288070 A1 * | 11/2008 | Lo | A61B 17/0401 623/13.13 |
| 2010/0069958 A1 | 3/2010 | Sullivan et al. | |
| 2010/0331896 A1 | 12/2010 | Le Couedic et al. | |

OTHER PUBLICATIONS

International Search Report issued in PCT/IB2020/052859, mailed Jul. 9, 2020, 10 pages.

* cited by examiner

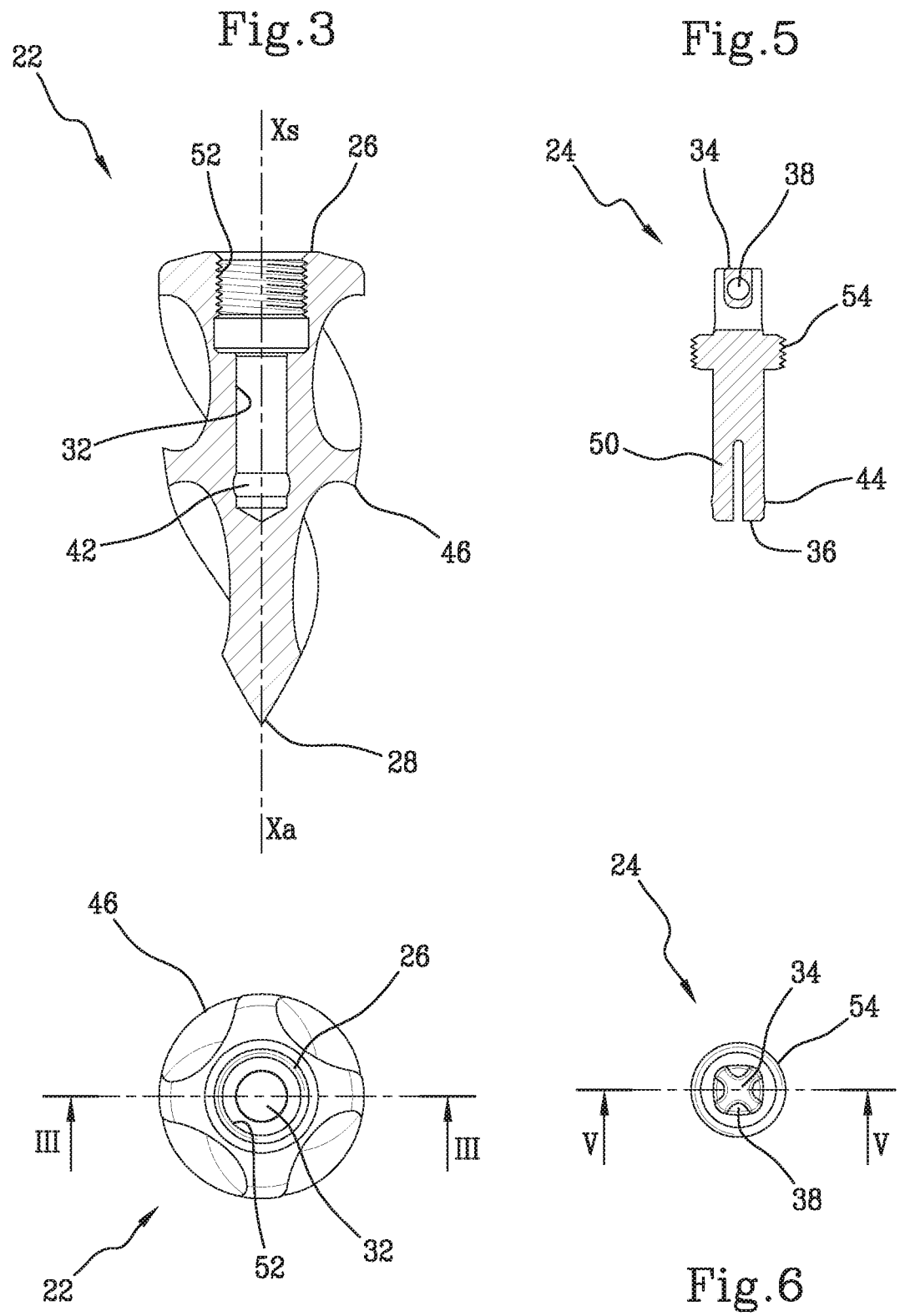

BONE ANCHORING ASSEMBLY

The present invention relates to a bone anchoring assembly comprising a rotatable insert, in particular an insert that can freely rotate in an anchor without running the risk of disassembly from it.

In bone surgery, soft tissue is known to be attached to a bone by means of a bone anchor and one or more suture threads. The bone anchor is shaped in such a way as to be able to be inserted into the bone and to be able to define with it a firm and stable coupling. The bone anchor further includes one or more eyelets to house suture threads intended to be bond to the soft tissue to be attached to the bone. It is preferable that, once the anchor is installed, the eyelets do not protrude with respect to the surface of the bone, but, on the contrary, remain within the original surface of the bone. For this reason, it is far more advantageous that the suture threads have passed through the eyelets before installing the anchor, otherwise this simple operation can be complicated and can take a long time, unnecessarily lengthening the surgery.

This solution, although widely spread and appreciated, is not completely without drawbacks.

Bone anchors can have different shapes. There are, for example, anchors that must be screwed, by means of a special tool, and other anchors (called impaction anchors) that instead, thanks to the particular shape of the thread, can be inserted into the bone simply by means of a hammer. In any case, attaching the anchor to the bone implies a rotation of the anchor around its own longitudinal axis. This rotation of the anchor also involves the rotation of the suture threads attached thereto, and this can easily lead to their twisting, which is extremely annoying for the purpose of the intervention.

Therefore, the object of the present invention is to overcome the drawbacks underlined before with respect to the prior art.

More specifically, it is a task of the present invention to provide a bone anchoring assembly, wherein the suture threads can rotate freely with respect to the bone anchor.

Furthermore, it is an object of the present invention to provide a bone anchoring assembly which, in addition to introducing new advantages, maintains substantially all advantages already obtained from known type anchors.

This object and tasks are achieved by means of a bone anchoring assembly according to claim 1.

To better understand the invention and appreciate its advantages, some of its exemplifying and non-limiting embodiments are described below with reference to the accompanying drawings, wherein:

FIG. 3 shows a view of the section made along the line III-III of FIG. 4;

FIG. 4 shows an axial view of the proximal end of a bone anchor according to the invention;

FIG. 5 shows a view of the section made along the line V-V of FIG. 6;

FIG. 6 shows an axial view of the proximal end of an anchor insert of FIGS. 3 and 4;

Figure 1:
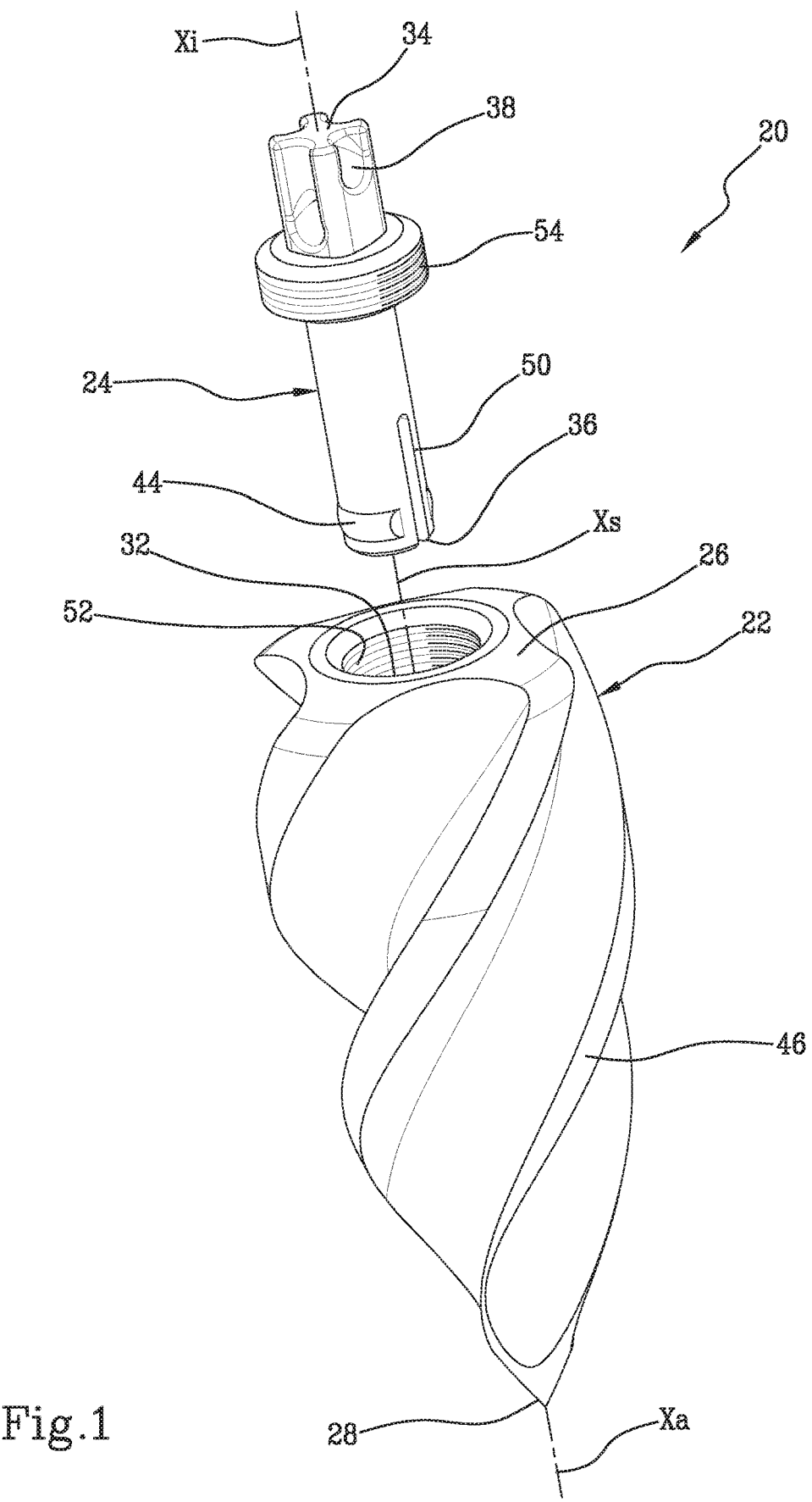
FIG. 1 shows a perspective view of an anchoring assembly according to the invention, in a disassembled configuration.

In the context of the present discussion, some terminological conventions have been adopted in order to make reading easier and smoother. These terminological conventions are clarified below with reference to the appended figures.

The invention comprises elements each defining univocally its own axis.

With respect to its own axis, the axial, radial and circumferential directions are defined for each element. Moreover, in some configurations of the invention, different elements may assume reciprocal positions in which the axes coincide with each other.

The invention comprises elastic elements. In relation to these elastic elements, the condition in which no significant external forces act on the elastic element is defined as unstrained condition.

As usual in surgery, the terms proximal and distal are used below.

Proximal refers to a position that, during correct use of the element to which it refers, is relatively close to the user. Typically, with reference to a bone anchoring, the proximal part is the one closest to the surgeon during implantation. Conversely, distal refers to a position that, during correct use of the element to which it refers, is relatively far from the user. Typically, with reference to a bone anchoring, the distal part is the one that is farthest from the surgeon during implantation.

The invention relates to a bone anchoring assembly generally referred to with 20. The bone anchoring assembly 20 comprises a bone anchor 22 and an insert 24. The bone anchor 22 comprises:
- a proximal end 26
- a distal end 28
- an outer profile suitable for defining a firm and stable coupling with the bone tissue 30, and
- a seat 32 open on the proximal end 26, wherein the seat 32 defines an axis Xs.

The insert 24 defines an axis Xi, is suitable for being received in the seat 32 of the bone anchor 22 and comprises:
- a proximal end 34;
- a distal end 36; and
- one or more eyelets 38 provided at the proximal end 34.

Moreover, the seat 32 and the insert 24 comprise snap coupling means 40 suitable for axially retaining the insert 24 in the seat 32 and suitable for allowing the free rotation of the insert 24 in the seat 32 around axis Xi.

Snap coupling means 40 suitable for being implemented in the invention are widely known to the skilled person. A particular embodiment is described below, with reference to the accompanying figures.

Preferably, in the bone anchoring assembly 20 according to the invention, the snap coupling means 40 comprise a circumferential groove 42 in the seat 32 and one or more radial nubs 44 provided elastically on the insert 24. For example, the radial nubs 44 of the insert 24 may assume at least one working configuration and one assembly configuration, wherein:
- in the working configuration the radial nubs 44 have radial protrusion larger than the portion of the insert 24 immediately next in the proximal direction and are adapted to engage the circumferential groove 42 of the seat 32 of the bone anchor 22; while
- in the assembly configuration the radial nubs 44 have radial protrusion reduced with respect to the working configuration, such that they can slide along the seat 32 of the bone anchor 22 so as to access the circumferential groove 42.

The outer profile of the bone anchor 22, in a manner known per se, may comprise a thread 46 suitable for defining a firm and stable coupling with a bone tissue 30. For example, the thread 46 may be of the type intended to be screwed into the bone tissue 30 by a tool imposing a rotation of the entire bone anchor 22. Alternatively, the thread 46 may be of the type intended to be introduced into the bone tissue 30 by percussion by means of a hammering mass.

Preferably also the entire bone anchor 22 as a whole defines an axis Xa and even more preferably the axis Xa of the bone anchor 22 coincides with the axis Xs of the seat 32. The embodiments depicted in the accompanying figures adopt this specific configuration.

As already mentioned, the insert 24 also defines its own axis Xi. In order to introduce the insert 24 into the seat 32 of the bone anchor 22, the axis Xi of the insert 24 must be made to coincide with the axis Xs of the seat 32.

Figure 2:
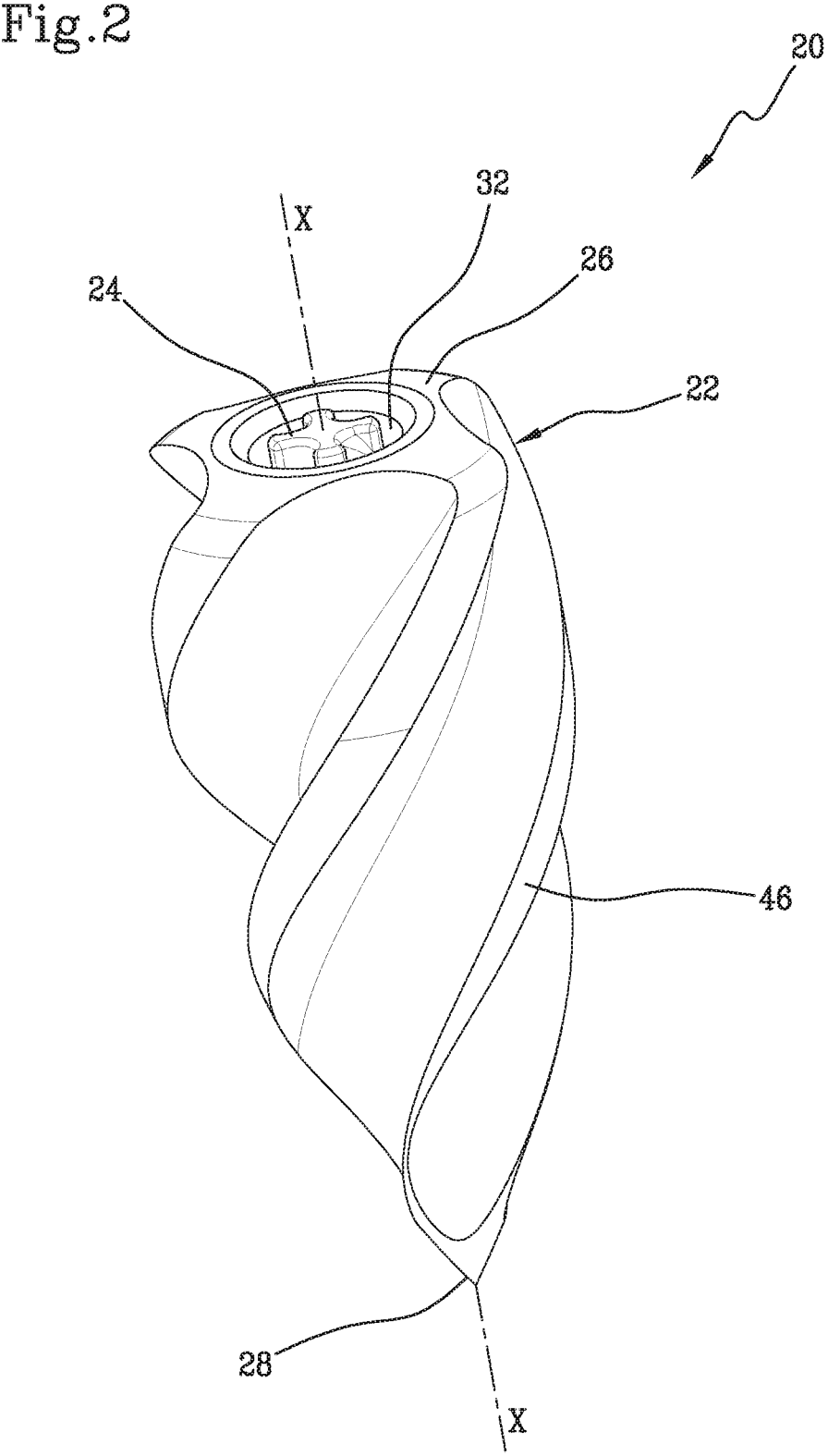
FIG. 2 shows the anchoring assembly of FIG. 1 in an assembled configuration.
Figure 7:
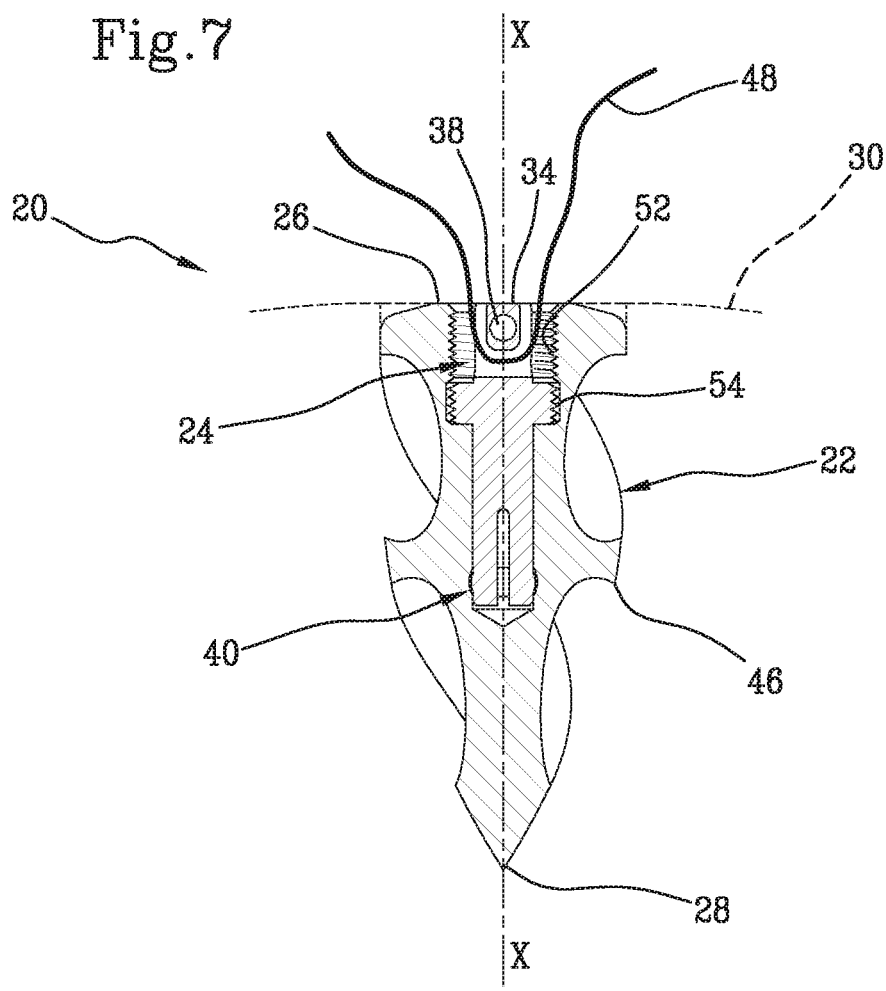
FIG. 7 shows view of the section made along the line VII-VII of FIG. 8.
Figure 8:
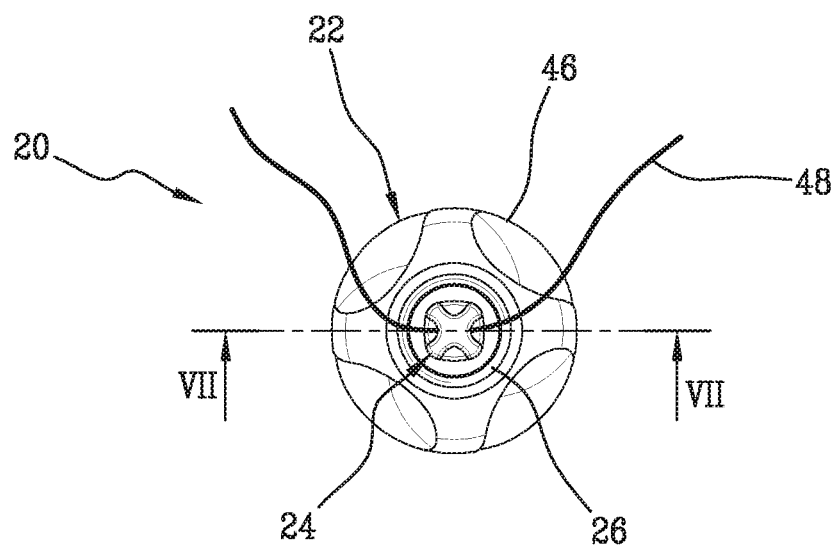
FIG. 8 shows an axial view of the proximal end of the bone anchor of FIGS. 3 and 4 and of the insert of FIGS. 5 and 6, in an assembled configuration.

In such a case, and when the bone anchoring assembly 20 is in its assembled configuration, it is possible to refer to a single axis X, without any lack of clarity. In the specific embodiments of the accompanying figures (see for example FIGS. 1, 2, 7, and 8) the only axis X is shared by the bone anchor 22, the seat 32, and the insert 24.

In a manner known per se, the eyelets 38 are adapted to define a firm anchoring for suture threads 48.

Preferably, as for example in the embodiments depicted in the accompanying figures, the radial nubs 44 are provided so that in the unstrained condition they spontaneously assume the working configuration. Conversely, in such embodiments, a radial force directed toward the axis X is required to bring the radial nubs 44 into the assembly configuration.

In the specific embodiment of the accompanying figures (see in particular FIGS. 1, 5 and 7), the insert 24 and its radial nubs 44 are made in a single piece. In particular, the insert 24 comprises a plurality of fingers 50 that cantilever in an axial direction and carry the radial nubs 44. In the unstrained condition the fingers 50 are separated from each other by a space. Thus, an adequate radial force directed toward the axis X may approach each other's fingers 50 and thereby reduce the radial protrusion of the radial nubs 44, bringing the insert 24 into the assembly configuration. During assembly of the bone anchoring assembly 20, the insert 24 is introduced into the seat 32 of the bone anchor 22 along the axial direction. During this step, at least in the section immediately proximal to the circumferential groove 42, the radial nubs 44 contact the walls of the seat 32 and are forced into the assembly configuration. When the radial nubs 44 reach the circumferential groove 42 they resume the working configuration, resulting in snap coupling between the insert 24 and the bone anchor 22. In particular, the coupling thus obtained determines a constraint in the axial direction that opposes the extraction of the insert 24 from the seat 32, while allowing the free rotation of the radial nubs 44 in the circumferential groove 42 and thus the free rotation of the insert 24 in the seat 32. In this manner, the assembled configuration of the bone anchoring assembly 20 is obtained.

According to some embodiments, such as, for example, those depicted in the accompanying figures, the seat 32 and the insert 24 each comprise a threaded portion 52 and 54. The threaded portion 52 of the seat 32 is provided in proximity of the proximal end 26 of the bone anchor 22. The threaded portion 54 of the insert 24, suitable to couple with the threaded portion 52 of the seat 32, is preferably positioned immediately distal to the eyelets 38.

In the event that the threaded portions 52 and 54 are provided, the assembly of the bone anchoring assembly 20 takes place as follows. The insert 24 is arranged such that its axis Xi coincides with the axis Xs of the seat 32. Then the insert 24 is introduced into the seat 32 until the thread 54 of the insert 24 is engaged with the thread 52 of the seat 32. Applying a relative rotation between the bone anchor 22 and the insert 24, the two threads 52 and 54 slide into each other so that the insert 24 enters further into the seat 32, distally.

Preferably, when the bone anchoring assembly 20 is in the assembled configuration, the proximal end of the threaded portion 54 of the insert 24 is immediately distal to the distal end of the threaded portion 52 of the seat 32. This type of solution is clearly seen in FIG. 7 and, during the last turns during which the threads 52 and 54 are still engaged with each other, allows the radial nubs 44 to be already proximal to the circumferential groove 42. Preferably, at the same time as the radial nubs 44 and the circumferential groove 42 cause snap coupling, the two threads 52 and 54 decouple from each other. In this way, the insert 24 remains constrained inside the seat 32 of the bone anchor 22. In fact, the axial constraint, defined by the radial nubs 44 engaging the circumferential groove 42, prevents the two threads 52 and 54 from coupling again and thus prevents the insert 24 from being extracted from the seat 32.

When the bone anchoring assembly 20 is in the assembled configuration, the insert 24 can freely rotate in the seat 32 relative to the bone anchor 22, without being extractable.

Preferably, when the bone anchoring assembly 20 is in the assembled configuration, the eyelets 38 are comprised axially in the profile of the proximal end 26 of the bone anchor 22. That is, when the bone anchoring assembly 20 is in the assembled configuration, the proximal end 34 of the insert 24 coincides with or is in a position immediately distal to the proximal end 26 of the bone anchor 22. As can clearly be seen in the example of FIG. 7, this feature results in the bone anchoring assembly 20 being properly implanted, without anything protruding beyond the profile of the bone tissue 30, with the only exception of the suture threads 48.

As the skilled person can easily understand, the invention allows to overcome the drawbacks highlighted previously with reference to the prior art.

In particular, the present invention provides a bone anchoring assembly 20 in which the suture threads 48 can rotate freely relative to the bone anchor 22.

Furthermore, the present invention provides a bone anchoring assembly 20 which, in addition to introducing new advantages, maintains substantially all the advantages already obtained from the anchors of the known type.

It is understood that the specific features are described in relation to different embodiments of the invention by way of non-limiting examples.

Obviously, one skilled in the art will be able to make further modifications and variations to the present invention, in order to satisfy contingent and specific needs. For example, the technical features described in relation to an embodiment of the invention may be extrapolated from it and applied to other embodiments of the invention. Such modifications and variations are also contained within the scope of the invention, as defined by the following claims.

The invention claimed is:

1. A bone anchoring assembly comprising:
   a bone anchor comprising:
      a proximal end;
      a distal end;

an outer profile suitable for defining a firm and stable coupling with a bone tissue;

a seat open on the proximal end, the seat comprising:
    a threaded portion comprising a proximal end and a distal end, wherein the proximal end of the threaded portion is provided in proximity to the proximal end of the bone anchor; and an insert configured to be received within and couple with the seat of the bone anchor, the insert comprising:
    a proximal end;
    a distal end;
    a threaded portion comprising a proximal end and a distal end, wherein the threaded portion of the insert is configured to couple with the threaded portion of the bone anchor; and
    wherein the insert is axially retained within the seat and is free to rotate about an axis of the insert, wherein when the bone anchoring assembly is in an assembled configuration, the proximal end of the threaded portion of the insert is in an immediately distal position with respect to the distal end of the threaded portion of the seat such that the threaded portions of the insert and seat threadingly disengage when in the assembled configuration, wherein the proximal end of the insert defines an eyelet, and wherein when the bone anchoring assembly is in the assembled configuration, the eyelet is disposed within the threaded portion of the bone anchor.

2. The bone anchoring assembly according to claim 1, wherein the bone anchor defines a circumferential groove distal to the threaded portion of the seat that couples with one or more radial nubs elastically provided on the insert when the bone anchoring assembly is in the assembled configuration, wherein the one or more radial nubs are disposed distally to the threaded portion of the insert.

3. The bone anchoring assembly according to claim 2, wherein the radial nubs of the insert are able to assume at least a working configuration and an assembly configuration, wherein:
    in the working configuration, the radial nubs have a radial protrusion larger than the portion of the insert immediately proximal the radial nubs and are adapted to engage the circumferential groove of the seat of the bone anchor; and
    in the assembly configuration, the radial protrusion is reduced with respect to the working configuration, such that the radial nubs are configured to slide along the seat of the bone anchor so as to access the circumferential groove.

4. The bone anchoring assembly according to claim 3, wherein the radial nubs are provided in such a manner that, in an unstrained condition, they spontaneously assume the working configuration.

5. The bone anchoring assembly according to claim 2, wherein the insert and its radial nubs are made in one single piece.

6. The bone anchoring assembly according to claim 1, wherein the threaded portion of the insert is provided in an immediately distal position with respect to the eyelet.

\* \* \* \* \*